United States Patent [19]

Howard, III

[11] Patent Number: 5,496,369
[45] Date of Patent: Mar. 5, 1996

[54] HUMAN CEREBRAL CORTEX NEURAL PROSTHETIC

[75] Inventor: Matthew A. Howard, III, Iowa City, Iowa

[73] Assignee: University of Iowa Research Foundation, Iowa City, Iowa

[21] Appl. No.: 194,017

[22] Filed: Feb. 9, 1994

[51] Int. Cl.⁶ .................................................... A61F 2/18
[52] U.S. Cl. ................................ 623/10; 623/11; 623/66
[58] Field of Search .............................. 623/10–12, 16, 623/24–25, 66

[56] References Cited

U.S. PATENT DOCUMENTS 5,000,194  3/1991  Honert et al. ............................... 623/10
5,271,397  12/1993  Segliman et al. .......................... 623/10

FOREIGN PATENT DOCUMENTS 0259906  3/1988  European Pat. Off. ................. 623/11

OTHER PUBLICATIONS

Center for Integrated Sensors and Circuits, "Passive Multi-channel Recording and Stimulating Electrode Arrays: A Catalog of Available Designs", Jul. 1991.
James P. Morgan, "The First Reported Case of Electrical Stimulation of the Human Brain," J. Hist. Med., Jan., 1982, pp. 51–63.
A. Earl Walker, "The Development of the Concept of Cerebral Localization in the Nineteenth Century," Bulletin His. Med., vol. 31, No. 2, Mar.–Apr., 1957, pp. 99–121.
Penfield et al., "Somatic Motor and Sensory Representation in the Cerebral Cortex of Man as Studied by Electrical Stimulation," Brain, vol. 60, 1937, pp. 389–443.
Penfield et al., "The Brain's Record of Auditory and Visual Experience," Brain, vol. 86, Dec. 1963, pp. 596–696.
Dobelle et al., "Artificial Vision for the Blind: Electrical Stimulation of Visual Cortex Offers Hope for a Functional Prosthesis," Science, vol. 183, 1974, pp. 440–444.
Dobelle et al., "A Prosthesis for the Deaf Based on Cortical Stimulation," Ann. Otol., vol. 82, 1973, pp. 445–463.
Cohen et al., "A Prospective, Randomized Study of Cochlear Implants," N.E. J. of Med., vol. 328, No. 4, Jan. 1993, pp. 233–237.
Eisenberg et al., "Electrical Stimulation of the Auditory Brain Stem Structure in Deafened Adults," J. Rehab. Research, vol. 24, No. 3, 1987, pp. 9–22.

*Primary Examiner*—Randall L. Green
*Assistant Examiner*—P. Zuttarelli
*Attorney, Agent, or Firm*—Mark L. Fleschner

[57] ABSTRACT

A neural prosthetic device for a primary auditory cortex of a patient includes a speech processor for receiving and processing audio information and for outputting processed electrical signals and a support arranged in said primary auditory cortex having a plurality of electrical contacts. The support is arranged in the patient's primary auditory cortex and each of the plurality of electrical contacts independently outputs electrical discharges in accordance with the processed electrical signals. The plurality of electrical contacts are arranged to approximately tonotopically match the primary auditory cortex.

18 Claims, 9 Drawing Sheets

HUMAN CEREBRAL CORTEX NEURAL PROSTHETIC

BACKGROUND OF THE INVENTION

1. Field of the Invention

This invention relates generally to an apparatus and method for treating a hard-of-hearing or deaf patient whose hearing cannot be restored with a cochlear implant, and in particular, to a human cerebral cortex neural prosthetic for delivering electrical signals to the patient's primary auditory cortex.

2. Background of the Related Art

Prior to the nineteenth century, physicians and scientists believed the brain was an organ with functional properties distributed equally through its mass. Localization of specific functions within subregions of the brain was first demonstrated in the 1800s, and provided the fundamental conceptual framework for all of modern neuroscience and neurosurgery. As it became clear that brain subregions served specific functions such as movement of the extremities, and touch sensation, it was also noted that direct electrical stimulation of the surface of these brain regions could cause partial reproduction of these functions. Morgan, J. P., "The first reported case of electrical simulation of the human brain," *J. History of Medicine*, January 1982:51–63, 1982; Walker, A. E., "The development of the concept of cerebral localization in the nineteenth century," *Bull. Hist. Med.*, 31:99–121, 1957.

The most extensive work on electrical stimulation "mapping" of the human brain surface was carried out over several decades by Dr. Wilder Penfield, a neurosurgeon and physiologist at the Montreal Neurological Institute, mostly during the early to mid-1900s. He made precise observations during cortical stimulation of hundreds of awake patients undergoing brain surgery for intractable epilepsy. Among his many findings, he noted that stimulation of the visual and hearing areas of the brain reproducibly caused the patients to experience visual and auditory phenomena. Penfield, W. et al., "Somatic motor and sensory representation in the cerebral cortex of man as studied by electrical stimulation," *Brain* 60:389–443, 1937; Penfield, W. et al., *Epilepsy and the Functional Anatomy of the Human Brain*, London-:Churchill, 1954; Penfield, W. et al., "The brain's record of auditory and visual experience," *Brain*, 86:595–696, 1963. Following the results of early human brain mapping studies, electrical stimulation of sensory brain regions to restore lost function was a logical therapeutic extrapolation. Drs. Brindley and Lewin of the University of Cambridge were the first to reduce the concept to practice by implanting a patient with a visual cortex neural prosthetic device. Brindley, G. S. et al., "The sensations produced by electrical stimulation of the visual cortex," *J. Physiol.* 196:479–493, 1968. Their device consisted of an array of thin, flat electrodes placed on the surface of the visual cortex. The electrodes were remotely controlled with radio signals. A similar system was later tested at the University of Utah by Dr. Dobelle and colleagues. Dobelle, W. H. et al., "Artificial vision for the blind: stimulation of the visual cortex offers hope for a functional prosthesis," *Science* 183:440–444, 1974.

Findings from these early British and American studies were consistent. Patients reliably perceived flashes of light (phosphenes) during periods of electrical stimulation, and simple patterns of phosphenes could be generated by simultaneously activating multiple contacts. While these findings strongly suggested the eventual feasibility of a cortical visual prosthetic device, many important design problems were insurmountable at that time.

Among these were an inability to precisely stimulate very small volumes of brain, the requirement for high stimulation currents to induce phosphenes, and an inability to access the patient's full "visual space" with the large array of surface electrodes used. Additionally, there were no miniature video cameras and small, powerful computers at the time capable of converting visual images into complex electrical stimulation sequences at ultra high speed.

The University of Utah has discontinued visual cortex prostheses research. However, the concept has been pursued at NIH where significant additional advances have been made. Their most important discovery to date relates to the use of needle shaped penetrating depth electrodes instead of flat surface stimulating electrodes. Bak, M., et al., "Visual sensations produced by intracortical microstimulation of the human occipital cortex," *Med. Biol. Eng. Comput.*, 28:257–259, 1990. Penetrating electrodes represent a major design improvement. They are placed within the brain tissue itself so there is optimal surface contact with elements of the brain that are targeted for stimulation. As a result, patients perceive visual phosphenes with approximately a thousand-fold less stimulation current than that required when surface electrodes are used. This allows for safe, chronic stimulation of very small discreet volumes of brain.

Additionally, penetrating electrodes transform what was in the past a two dimensional implant-brain interface (flat disks on the surface of the brain) into a three dimensional interface (multiple needle-like electrodes in parallel extending from the surface into the brain substance), which vastly increases the device's access to stimulation targets below the surface. To use a television screen analogy, a two dimensional surface-electrode array may have the potential of generating an image on the "screen" composed of approximately one hundred discreet dots ("pixels"), whereas a three-dimensional array would potentially generate an image with many thousands of dots. The huge potential increase in image resolution would be achieved using a small fraction of the stimulation currents used in the past.

Penetrating electrodes have the potential to markedly increase both image quality and the safety of the stimulation process. Human experimental studies continue at the NIH campus. Extramural NIH funding is also directed at supporting engineering research on penetrating electrodes optimally suited for neural prosthetics applications. The University of Michigan, for example, has made use of computer-chip manufacturing techniques to synthesize exquisitely small electrode arrays. The etched electrical contacts on these devices are so small that the distance separating adjacent contacts can be in the range of 50 micrometers, approximately the diameter of two nerve cell bodies. Drake, K. L. et al., "Performance of planar multisite microprobes in recording extracellular single-unit intracortical activity," *IEEE Trans. BME*, 35:719–732, 1988.

During the 1970s the neural prosthetics group at the University of Utah not only explored the feasability of a visual cortex neural prosthetic device, but carried out experiments in auditory cortex stimulation as well. Led by Dr. Dobelle, they formed a mobile research group that traveled to surgical centers throughout the United States when suitable experimental subjects were identified. These were patients who required temporal lobe surgery for tumor removal or treatment of intractable epilepsy, and who agreed to participate in the experimental protocol. Dobelle, W. H. et al., "A prosthesis for the deaf based on cortical stimulation," *Ann. Otol*, 82:445–463, 1973.

The primary auditory region of the human brain is buried deep within the sylvian fissure. It is not visible from the brain surface and its exact location varies slightly from one person to the next. MRI and CT scanners were not invented at the time of Dr. Dobelle's experiments so the anatomy of the patients' auditory cortex could not be studied prior to surgery, and this region could only be visualized with difficulty in the operating room after the Sylvian fissure was surgically dissected. Once the buried auditory cortex was exposed, surface stimulating electrodes were placed by hand over the area thought to be auditory cortex and the brain was stimulated in a fashion similar to that used to generate visual phosphenes.

Reproducible sound sensations were generated in the experimental subjects. Though these preliminary findings were encouraging, a range of limitations precluded further work by this group. Among the more daunting problems the Utah group faced were recruiting suitable patients for the experimental study and obtaining good stimulation characteristics from the experimental surface electrodes. The minimal stimulation threshold for eliciting sound sensations was found to be 6 milliamperes, which is too high to be tolerated chronically and is thousands of times greater than currents found subsequently to be required to generate phosphenes in visual cortex using penetrating electrodes.

Recent advances in MRI and computer technology now allow detailed preoperative imaging of human auditory cortex.

Another major technical innovation developed since the time of Dr. Dobelle's early experiments is the cochlear implant. An important aspect of the cochlear implant technology, which is now highly refined, involves transducing sound into complex electrical stimulation sequences. This large body of technical knowledge developed over the last twenty years will be directly applicable to the auditory cortex prosthetic device and aid immeasurably in its research and development.

Normal Hearing

Mechanisms of human hearing are reviewed briefly to provide a framework for discussion of auditory neural prosthetic devices. The auditory system is composed of many structural components that are connected extensively by bundles of nerve fibers. The system's overall function is to enable humans to extract usable information from sounds in the environment. By transducing acoustic signals into electrical signals that can then be processed in the brain, humans are able to discriminate amongst a wide range of sounds with great precision.

Figure 1A:
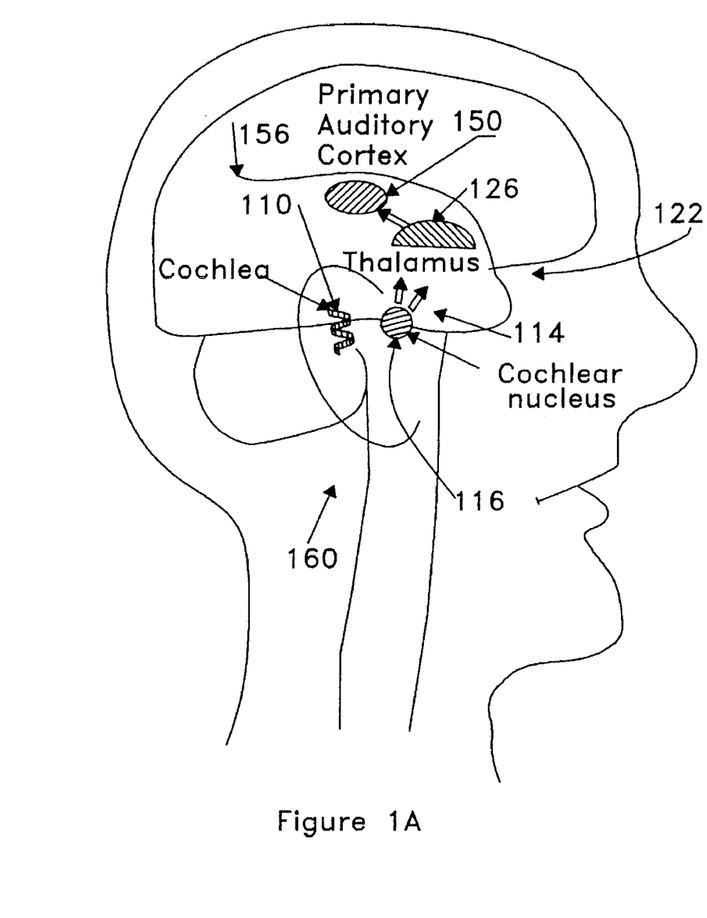
FIGS. 1A and 1B show the orientation of a patient's primary auditory cortex in relation to the patients cochlea and cochlear nucleus.
Figure 1B:
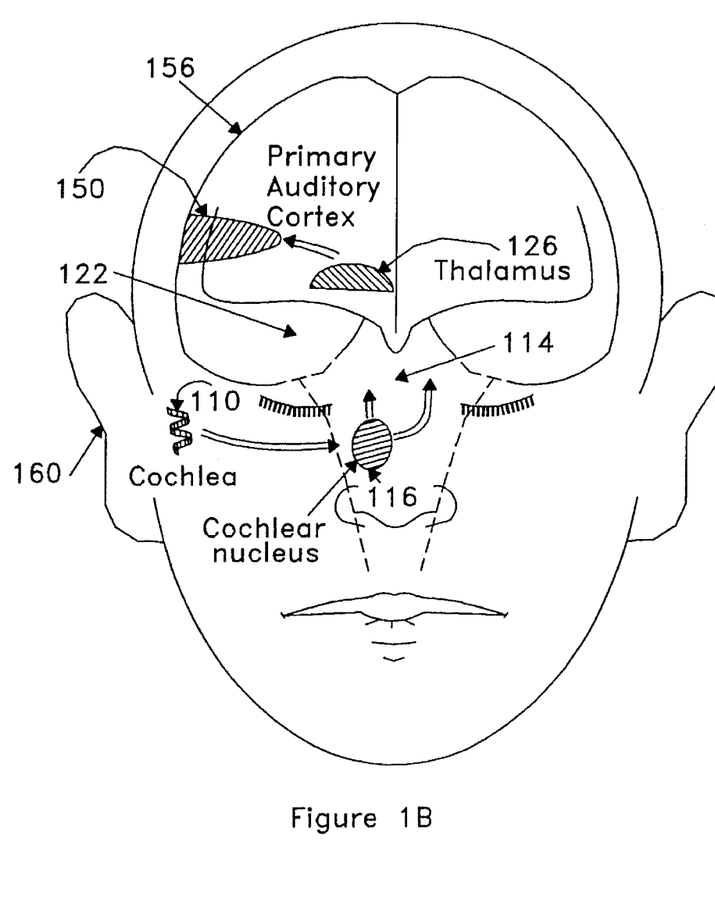

FIGS. 1A and 1B show a side and front view of areas involved in the hearing process. In particular, the normal transduction of sound waves into electrical signals occurs in cochlea 110, a part of the inner ear located within temporal bone (not shown). Cochlea 110 is tonotopically organized, meaning different parts of cochlea 110 respond optimally to different tones; one end of cochlea 110 responds best to high frequency tones, while the other end responds best to low frequency tones. Cochlea 110 converts the tones to electrical signals which are then received by cochlea nucleus 116. This converted information is passed from cochlea 110 into brain stem 114 by way of electrical signals carried along the acoustic nerve and in particular, cranial nerve VIII (not shown).

The next important auditory structure encountered is cochlea nucleus 116 in the brain stem 114. As the acoustic nerve leaves the temporal bone and enters skull cavity 122, it penetrates brain stem 114 and relays coded signals to cochlear nucleus 116, which is also tonotopically organized. Through many fiber-tract interconnections and relays (not shown), sound signals are analyzed at sites throughout brain stem 114 and thalamus 126. The final signal analysis site is auditory cortex 150 situated in temporal lobe 156.

The mechanisms of function of these various structures has also been extensively studied. The function of cochlea 110 is the most well-understood and the function of auditory cortex 150 is the least understood. For example, removal of the cochlea 110 results in complete deafness in ear 160, whereas removal of auditory cortex 150 from one side produces minimal deficits. Despite extensive neural connections with other components of the auditory system, auditory cortex 150 does not appear to be necessary for many auditory functions.

Cochlear Implant

Cochlear implants were designed for patients who are deaf as a result of loss of the cochlea's sound transduction mechanism. Implant candidates must have an intact acoustic nerve capable of carrying electrical signals away from the middle ear into the brain stem. The device converts sound waves into electrical signals which are delivered through a multi-contact stimulating electrode. The stimulating electrode is surgically inserted by an otolaryngologist into the damaged cochlea. Activation of the contacts stimulates acoustic nerve terminals which would normally be activated by the cochlear sound transduction mechanism. The patient perceives sound as the coded electrical signal is carried from the middle ear into the brain by the acoustic nerve. Cohen, N. L. et al., "A prospective, randomized study of cochlear implants," *N. Engl. J. Med.*, 328:233–7, 1993.

In patients with hearing loss caused by dysfunction at the level of the cochlea, cochlear implants can be remarkably effective in restoring hearing. For example, some previously deaf patients are able to understand conversations over the telephone following insertion of a cochlear implant.

Cochlear implants are surgically placed in the middle ear which is situated in the temporal bone. In patients who are already deaf, there is very little chance of any additional injury being caused by placement of a cochlear implant; they are very safe device. Because of the low health risk associated with placing cochlear implants, obtaining experimental subjects during the early development stage was not difficult. In this setting design improvements occurred rapidly.

Cochlear Nucleus Implant

Patients are not candidates for cochlear implants if their hearing loss results from damage in auditory regions other than the cochlea. Because the first auditory relay station "downstream" from the cochlea and auditory nerve is the brainstem cochlear nucleus, this structure is a logical candidate for consideration as an implantation site. This approach was first developed at the House Ear Institute. Eisenberg, L. S. et al., "Electrical stimulation of the auditory brainstem structure in deafened adults," *J. Rehab. Res.* 24:9–22, 1987; Hitselberger, W. E. et al., "Cochlear nucleus implant," *Otolaryngol. Head Neck Surg.*, 92:52–54, 1984. As is the case with cochlear implants, sound waves are translated into a complex electrical code F. The implant's stimulation terminals are placed up against the cochlear nucleus, and the patient perceives sounds when the system is activated.

Data on efficacy is limited because relatively few patients have been tested with this device. Early findings demonstrate, however, that some degree of useful hearing is restored using this device. Environmental sounds such as a knock at the door and a telephone ringing have been detected by patients with a cochlear nucleus implant, and this improved auditory function has increased patients' ability to live independently.

Although work in the visual cortex demonstrates that central nervous system penetrating electrodes are significantly more effective than surface electrodes, use of penetrating electrodes in the cochlear nucleus has been discontinued for safety reasons described below.

For several reasons, there is significantly more risk associated with cochlear nucleus implants than cochlear implants. The cochlear nucleus is situated in the brain stem; a very sensitive and vital structure. Neurosurgical procedures in the brain stem are among the most difficult and dangerous operations performed. Infiltrating tumors within the substance of the brainstem, for example, are usually considered surgically inoperable. Surgical manipulation or injury of brainstem elements can cause devastating complications, including loss of normal swallowing functions, loss of control of eye movements, paralysis, coma, and death.

Because of their internationally renowned acoustic neuroma practice, doctors at the House Ear Institute are among the most experienced surgeons in the world at gaining surgical access to the brainstem surface. Acoustic neuroma's are tumors arising from the supporting cells of the acoustic nerve. As they enlarge, these tumors expand into the cranial cavity and press up against the brainstem. Patients typically present with hearing loss, and a number of surgical approaches have been developed by otolaryngologists and neurosurgeons to remove these lesions.

Surgeons at the House Ear Institute have played a pioneering role in acoustic neuroma surgery and now routinely perform operations where the tumor is safely removed and the brainstem surface is visualized. They have placed cochlear nucleus implants in deaf patients who have lost function of both acoustic nerves and are undergoing removal of an acoustic neuroma. This affords access to the brainstem surface during a medically necessary procedure.

The first cochlear nucleus implant used penetrating electrodes. These functioned well initially, however within two months they had migrated further into the brainstem, causing tingling sensation in the patient's hip as adjacent fiber tracts were inadvertently stimulated. This system was removed and surface electrodes have been used for cochlear nucleus implants since that time. Risks of implanting a cochlear nucleus device are such that patients are only candidates for implantation if they require surgery in that area of the brainstem for some other, usually life threatening reason.

It is difficult to find suitable patients for implantation and testing of cochlear nucleus implants. The most likely candidates are patients who have a rare form of neurofibromatosis and acoustic neuromas on both acoustic nerves. Martuza, R. L. et al., "Neurofibromatosis 2 (Bilateral Acoustic Neurofibromatosis)," *N. Engl. J. Med.*, 318:684–688, 1988. A small number of these patients are referred regularly to such institutions as the House Ear Institute. Many university medical centers, however, would be unable to identify a single suitable candidate during a full year. In the fourteen years since its initial clinical application at the House Institute, cochlear nucleus implant use and testing has remained quite restricted (less than two implants per year average during the epoch reported in Eisenberg, L. S. et al., "Electrical stimulation of the auditory brainstem structure in deafened adults," *J. Rehab. Res.* 24:9–22, 1987.

Treating Deafness

Devices designed to treat deafness must take into consideration the underlying cause of deafness. For example, a patient with defective cochlea 110 who still has a functional acoustic nerve, may benefit from an artificial cochlea (cochlear implant). However, if the acoustic nerve is damaged and cannot carry electrical signals, then the problem is "too far downstream" in the signal processing sequence for a cochlear implant to be effective. In that situation, artificial signals must enter the auditory system "beyond the block" either in brain stem 114 or in auditory cortex 150.

SUMMARY OF THE INVENTION

It is therefore an object of the invention to provide a prosthetic which can be placed in a cerebral cortex to reconstitute sensor input to the brain using microstimulation.

Another object of the invention is to provide a prosthetic which can be positioned in the brain such that an entire range of tonal frequencies processed by the human brain are accessed thereby.

Another object of the invention is to provide a prosthetic which allows a physician to physiologically test location and function of neural prosthetic electrodes in patients undergoing surgery for medically intractable epilepsy.

One feature of the invention is that it includes a penetrating longitudinal support or electrode.

Another feature of the invention is that it includes multiple contacts on the longitudinal support.

Another feature of the invention is that it includes a speech processor.

Another feature of the invention is that each contact can separately introduce electrical discharges in the primary auditory cortex.

Another feature of the invention is that it is arranged along the primary auditory cortex.

Another feature of the invention is that it can include a flexible wire multicontact electrode.

Another feature of the invention is that the flexible wire multicontact electrode is inserted into the brain using a rigid introducer.

Another feature of the invention is that a flat plastic plate attached to the longitudinal support helps position the prosthetic in the auditory cortex. The flat plastic plate having a cup to receive a sphere coupled to leads which interconnect the contacts to the speech processor.

One advantage of the invention is that it includes contacts which enable a deaf patient to hear even though the patient's problem is not in his or her cochlear regions but instead is farther "down stream."

Another advantage of the invention is that it can utilize a single electrode.

Another advantage of the invention is that it penetrates the brain thus requiring significantly less current to stimulate localized areas of the auditory cortex.

Another advantage of the invention is that the contacts are sufficiently closely arranged next to each other to provide high resolution stimulation of the auditory cortex.

These and other objects, advantages and features are accomplished by the provision of a neural prosthetic device for a primary auditory cortex of a patient, including: a speech processor for receiving and processing audio information and for outputting processed electrical signals, a support arranged in the primary auditory cortex having a plurality of electrical contacts, the support being arranged in the primary auditory cortex and each of the plurality of electrical contacts independently outputting electrical discharges in accordance with the processed electrical signals; and electrical coupling means for electrically coupling the electrical contacts to the speech processor.

The above objects, advantages and features are further accomplished by the neural prosthetic apparatus as above, wherein the support is arranged in the primary auditory cortex and the plurality of electrical contacts are arranged such that the plurality of electrical contacts approximately tonotopically match the primary auditory cortex.

These and other objects, advantages and features are also accomplished by a method of implanting the above support, including the steps of: acquiring a 3 dimensional digital image of the patient's brain and storing the 3 dimensional digital image in a memory of a computer; digitally subtracting data from the 3 dimensional digital image to yield a modified 3 dimensional digital image which shows the orientation of the primary auditory cortex in the patient's brain; and inserting the support into the primary auditory cortex using the modified 3 dimensional digital image as a guide.

The above and other objects, advantages and features are further accomplished by the steps of: repeatedly outputting the processed electrical signals to the plurality of electrical contacts; and adjusting orientation of the support in the primary auditory cortex as the patient describes effects of the repeatedly outputting step.

These and other objects, advantages and features of the present invention will become more apparent from the following description of embodiments thereof taken in conjunction with the accompanying drawings.

DETAILED DESCRIPTION OF THE PREFERRED EMBODIMENT

Advanced imaging combined with an intraoperative stereotactic system now enable placement of penetrating electrodes into auditory cortex during routine epilepsy surgery without dissection of the Sylvian fissure.

Primary auditory cortex 150 in FIGS. 1A and 1B is tonotopically organized, meaning stimulation in different areas is likely to cause the patient to perceive different tones. These tones form the building blocks of complex sound phenomena such as speech. Tonotopic organization is a fundamental characteristic of the cochlea and cochlear nucleus as well, as discussed above. Auditory cortex 150, however, has its tonotopic map stretched across a larger volume of tissue (greater than twice the volume of cochlear nucleus 116). Greater tissue volume enables placement of a greater number of electrical contacts for a given tonotopic zone. This results in increased signal resolution and improved clarity of auditory sensation. Finally, because of anatomical differences, auditory cortex 150 can accommodate penetrating electrode arrays which cannot be safely placed into the cochlear nucleus.

Figure 2:
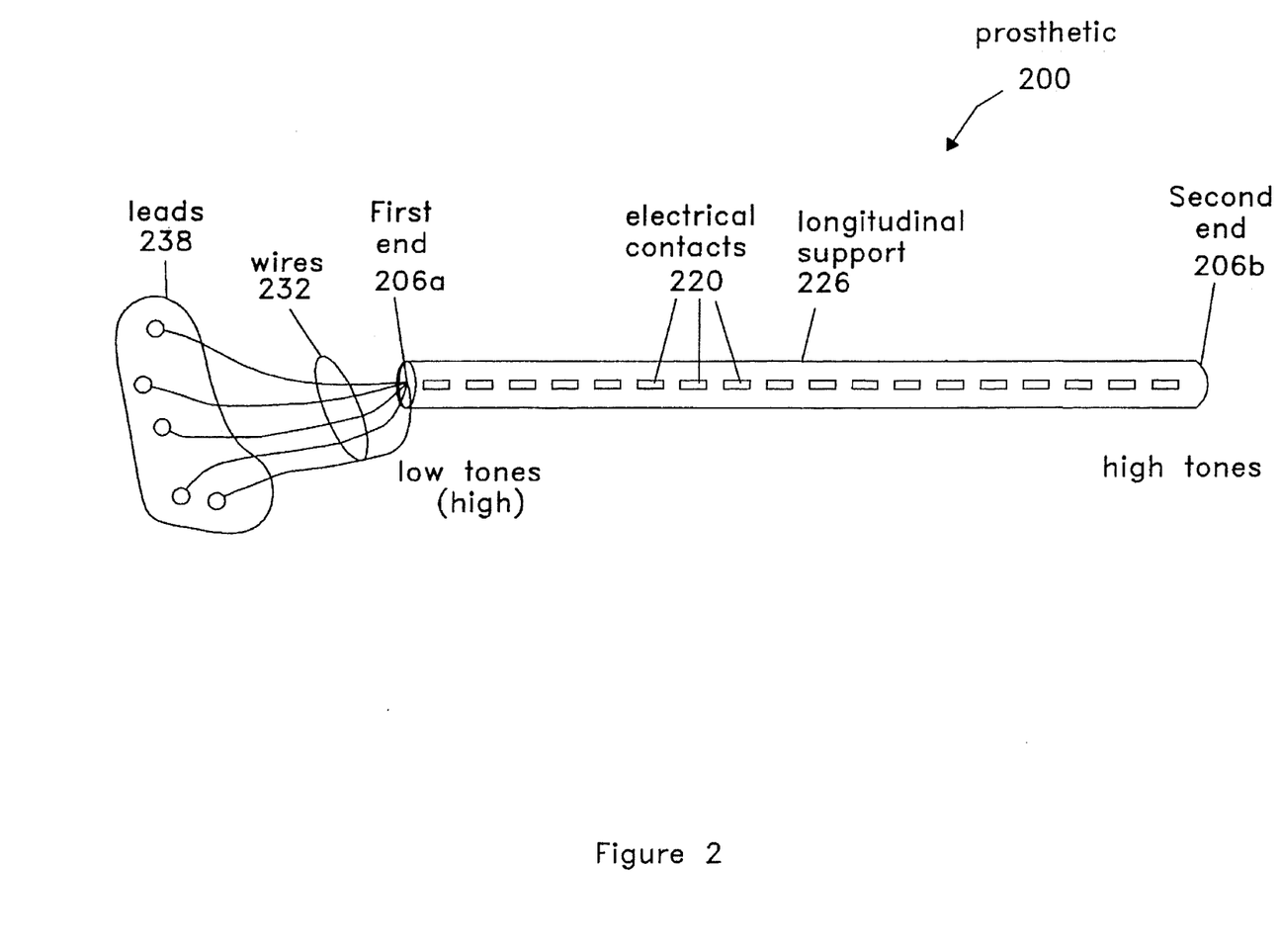
FIG. 2 shows a human cerebral cortex neural prosthetic according to one embodiment of the invention.

FIG. 2 shows a human cerebral cortex neural prosthetic 200 according to one embodiment of the invention. Prosthetic 200 has a first end 206a and a second end 206b which is blunt or smoothly curved. Prosthetic 200 has electrical contacts 220 along a longitudinal support 226. Support 226 can be anywhere from several millimeters long to several centimeters long. Electrical contacts 220 are small metal pads which can be separately electrically charged via respective wires 232 available at first end 206a. Wires 232 have leads 238 which are coupled to a speech processor (not shown). Electrical contacts 220 are spaced approximately 10 micrometers to several millimeters apart and preferably approximately 50 to 150 micrometers apart. Application of a voltage to contacts 220 near first end 206a results in stimulating low (or high—to be determined by questioning the patient) tones in auditory cortex 150 (see FIGS. 1A and 1B), whereas application of a voltage to contacts 220 near second end 206b results in stimulation of high (or low) tones in auditory cortex 150.

Longitudinal support 226 can be a rigid support or a flexible wire with a rigid introducer which enables the physician to introduce prosthetic 200 into a patient's brain and then subsequently remove the rigid introducer thereby exposing electrical contacts 220 to auditory cortex 150. Support 226 can be one of the probes shown in FIGS. 3–5 in "Passive Multichannel Recording and Stimulating Electrode Arrays: A Catalog of Available Designs" by the Center for Integrated Sensors and Circuits, University of Michigan Ann Arbor, Mich., the contents of which are incorporated herein by reference. Alternative electrodes such as Depthalon Depth Electrodes and interconnection cables from PMT Corporation 1500 Park Road, Chanhassen, Minn., 55317 could also be used as support 226 and electrical couplers between contacts 220 and a speech processor (410 in FIG. 4).

Electrical contacts 220 must operate as high impedance (megohms) contacts as opposed to low impedance (a few ohms to several thousand ohms) contacts as some of the electrodes. This enables the contacts to output a small (a few microamperes as apposed to a few milliamperes) current. This also localizes the potentials applied to the patient's primary auditory cortex to approximately a few hundred micrometers. The localization of applied electric charges corresponds to the tonotopic spacing of nerve cells.

Prosthetic 200 is arranged along a longitudinal direction of auditory cortex 150. However, auditory cortex 150 is located in the transverse temporal gyro and is buried deep within the Sylvian fissure. Consequently, its location cannot be determined simply by looking at an exposed surface of the brain. Therefore, MRI imaging techniques must be employed to reveal the exact orientation of auditory cortex 150.

A single coronal image of an individual's brain cannot reveal the exact orientation of auditory cortex 150. Instead, a series of images must be obtained and a resulting 3-D MRI image constructed. Once such an image is constructed, the digital data making up that image can be transformed to provide a complete 3-dimensional view of the Sylvian fissure. This in turn exposes auditory cortex 150 as a continuous raised mound, similar to a mole too. That is, tissue on top of the digital image can be "peeled off" to expose the sylvian fissure and consequently auditory cortex 150 "pops out" of the image. This process is described in "Three-dimensional In Vivo Mapping of Brain Lesions in Humans", by Hanna Damasio, MD, Randall Frank, the contents of which are incorporated herein by reference.

Figure 3A:
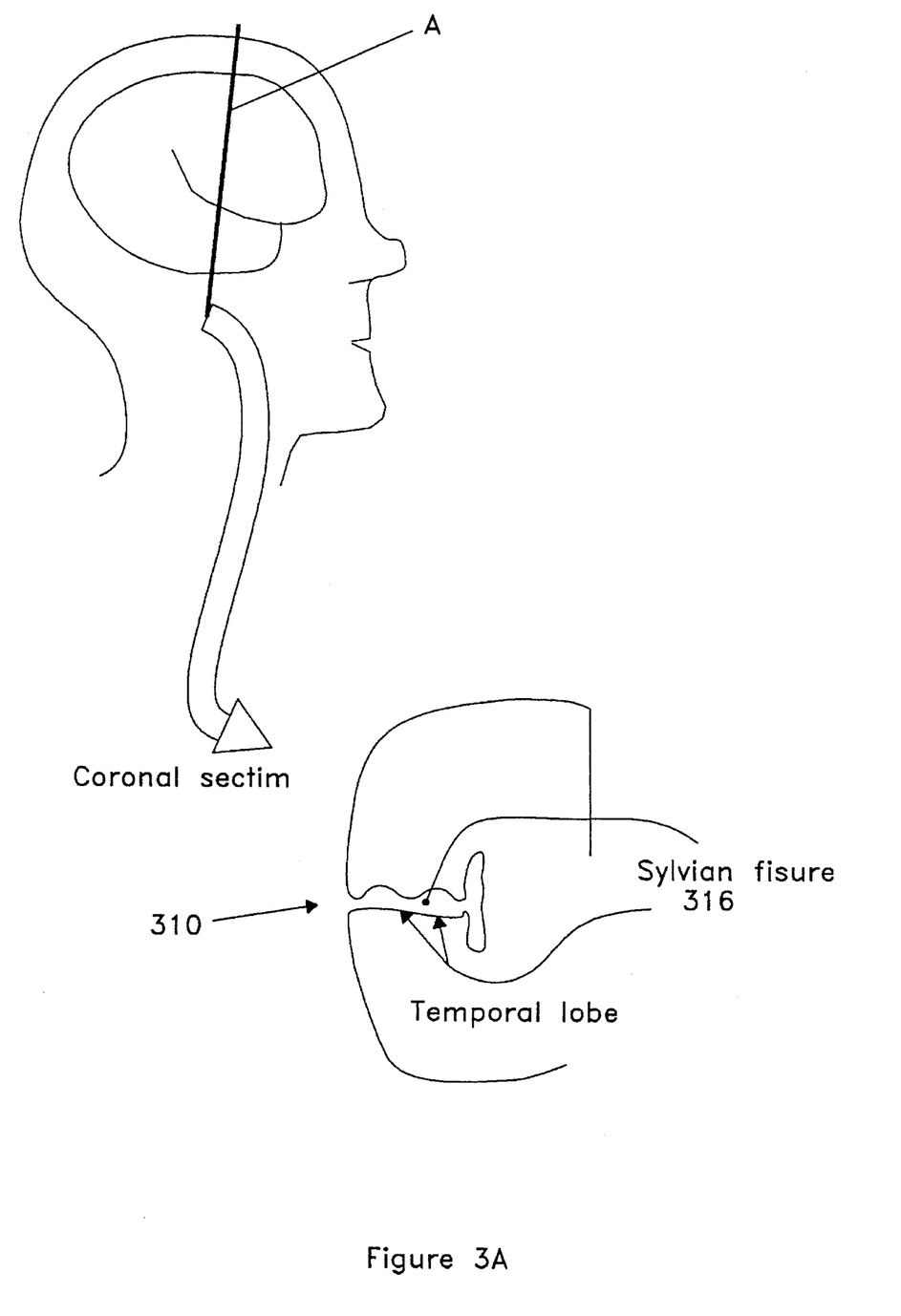
FIG. 3A shows a side view of a plane A which intersects a coronal section with a Sylvian fissure exposed.
Figure 3B:
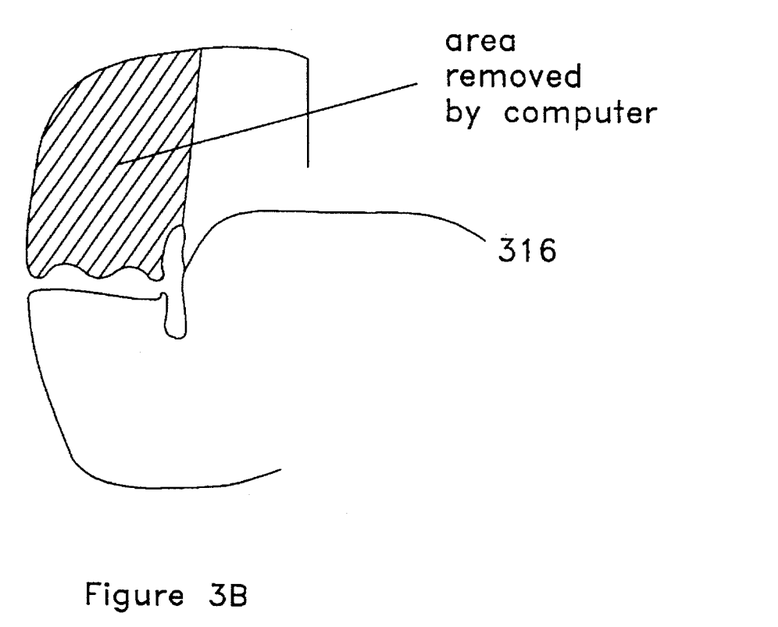
FIGS. 3B and 3C show the coronal section before and after tissue is digitally "peeled off" Sylvian fissure, and a view from above after the supra Sylvian tissue has been "peeled off".
Figure 3C:
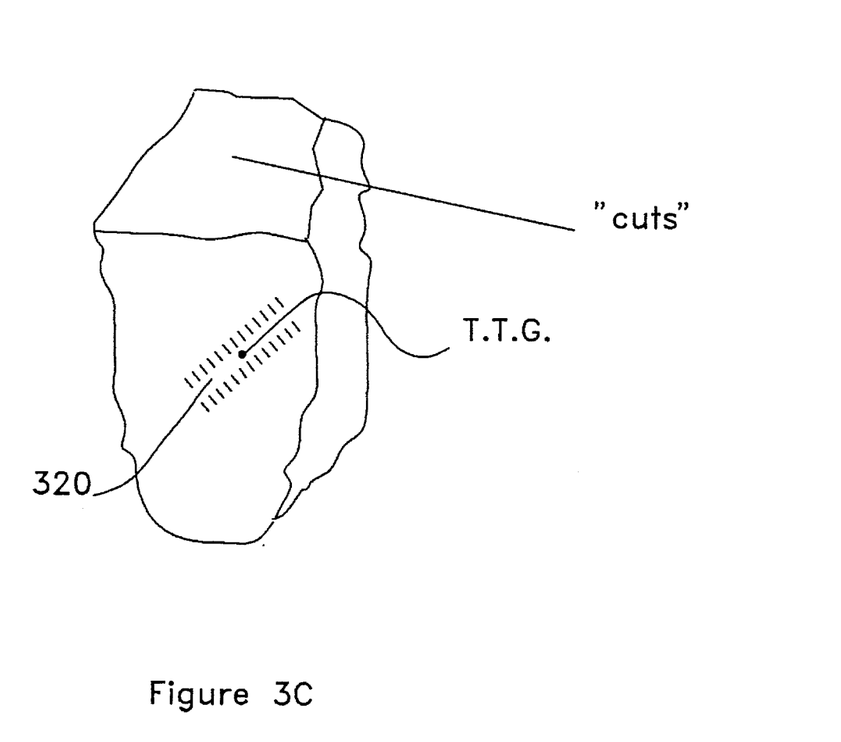

FIG. 3A shows a side view-of a plane A which intersects a coronal section 310 as well as a view of coronal section 310 with Sylvian fissure 316 exposed. FIGS. 3B and 3C show coronal section 310 before and after tissue is digitally "peeled off" to expose auditory cortex 150. One or more resulting mounds 320 is revealed in FIG. 3C and this mound corresponds to auditory cortex 150 of FIG. 1B. Mound 320 does not appear until after tissue on the underside of Sylvian fissure 316 is reconstructed to provide the 3-D image.

Figure 4:
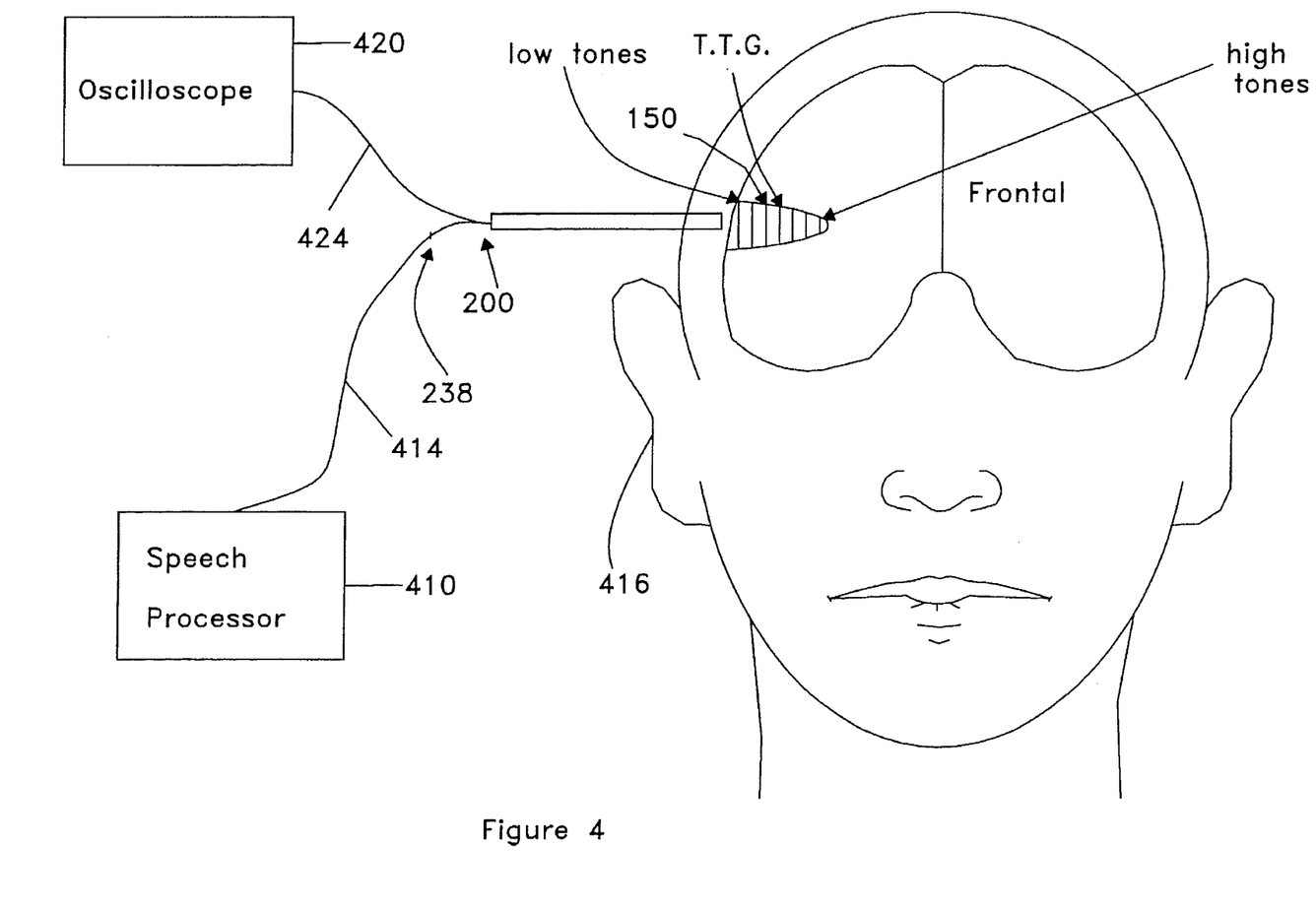
FIG. 4 shows a neural prosthetic with a support having electrical contacts and it's speech processor.

Once the exact location and orientation of mound 320 and consequently auditory cortex 150 have been determined using these 3-D MRI image processing techniques, the actual primary auditory cortex 150 can be localized in 3-dimensional space and prosthetic 200 can be accurately inserted into auditory cortex 150. FIG. 4 shows prosthetic 200 just prior to insertion into auditory cortex 150. In addition, FIG. 4 shows a speech processor 410 coupled to leads 238 via coupling cable 414. Examples of speech processors for speech processor 410 is Nucleus Device made by Cochlear Corporation. Speech processor 410 can be miniaturized and placed directly behind ear 416 in the patient's mastoid. FIG. 4 also shows additional diagnostic equipment including an oscilloscope 420 coupled to prosthetic 200 via cable 424.

Figure 5:
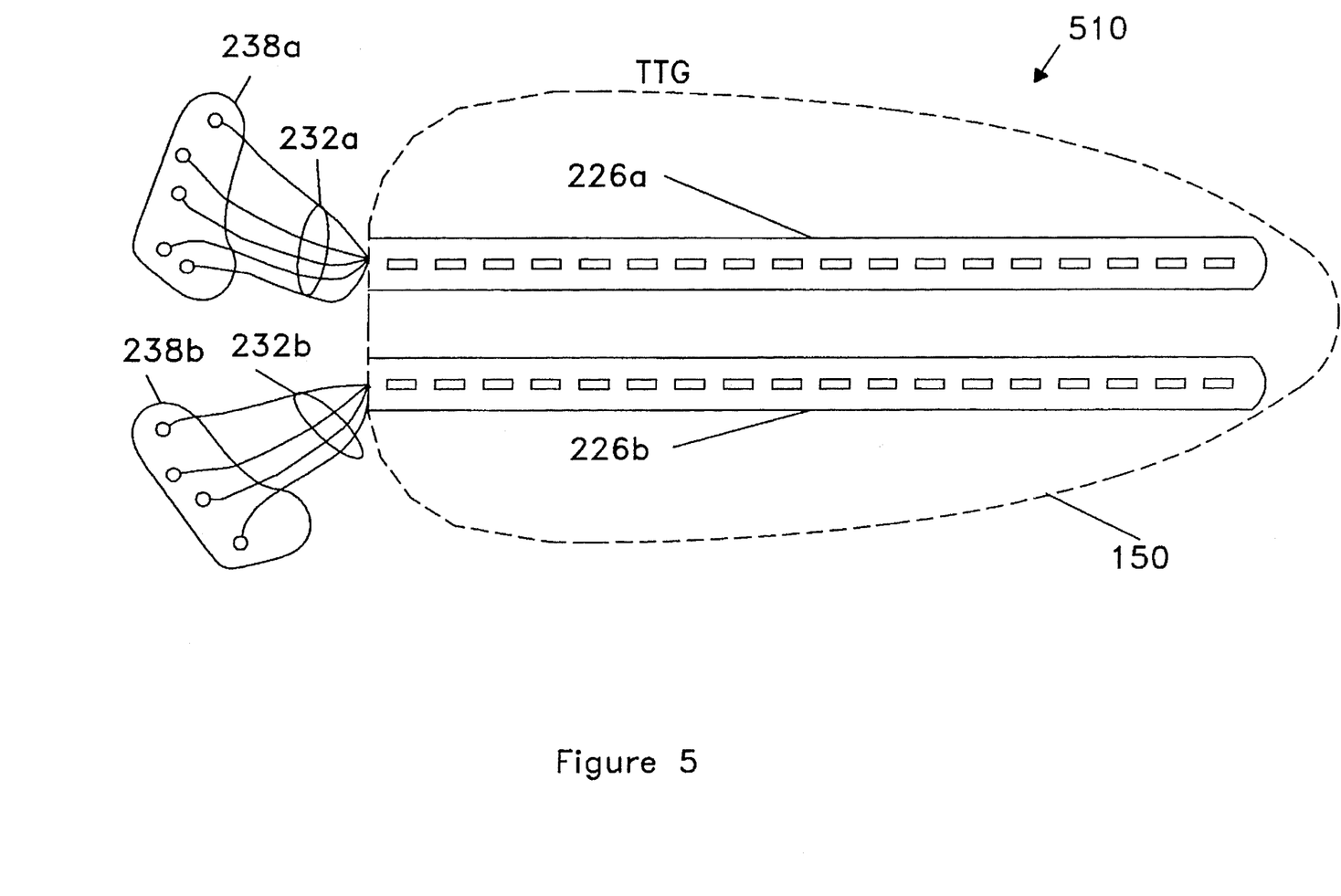
FIG. 5 shows a prosthetic which includes two longitudinal supports according to another embodiment of the invention.

FIG. 5 shows a prosthetic 510 which includes two longitudinal supports 226a and 226b according to another embodiment of the invention. Although two supports are shown, three or more such supports could be used. Longitudinal support 226a has wires 232a with corresponding leads 238a and longitudinal support 226b has wires 232b and leads 238b. Leads 238a and 238b are again connected to speech processor 410 as in FIG. 4. In addition, scope 420 can be used to observe signals output to longitudinal support 226a and 226b.

Figure 6:
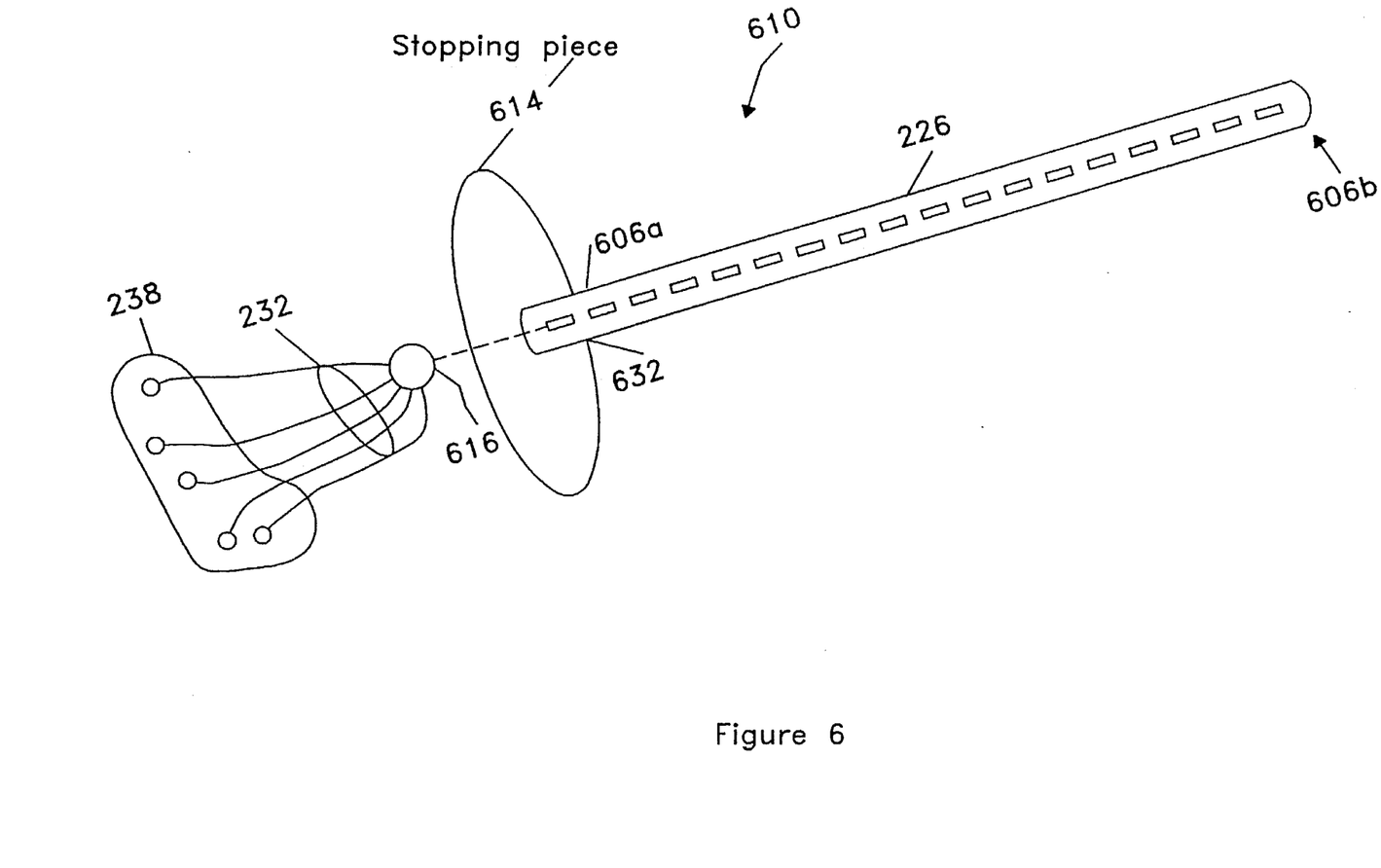
FIG. 6 shows a prosthetic according to yet another embodiment of the invention.

FIG. 6 shows a prosthetic 610 according to yet another embodiment of the invention. In particular, FIG. 6 shows longitudinal support rod 226 with first end 606a and second end 606b. End 606a is arranged in the region of auditory cortex 150 with low tones (or high tones as previously discussed) and second end 606b is arranged in the region of auditory cortex 150 with high (or low) tones in a manner similar to first end 206a and second end 206b of FIG. 2. Here, however, longitudinal support 226 has a sphere 616 which is stopped by a stopping piece 614. This enables the physician to insert longitudinal support 226 at a wide range of angles and yet secure prosthetic 610 once longitudinal support 226 has been inserted.

Figure 7A:
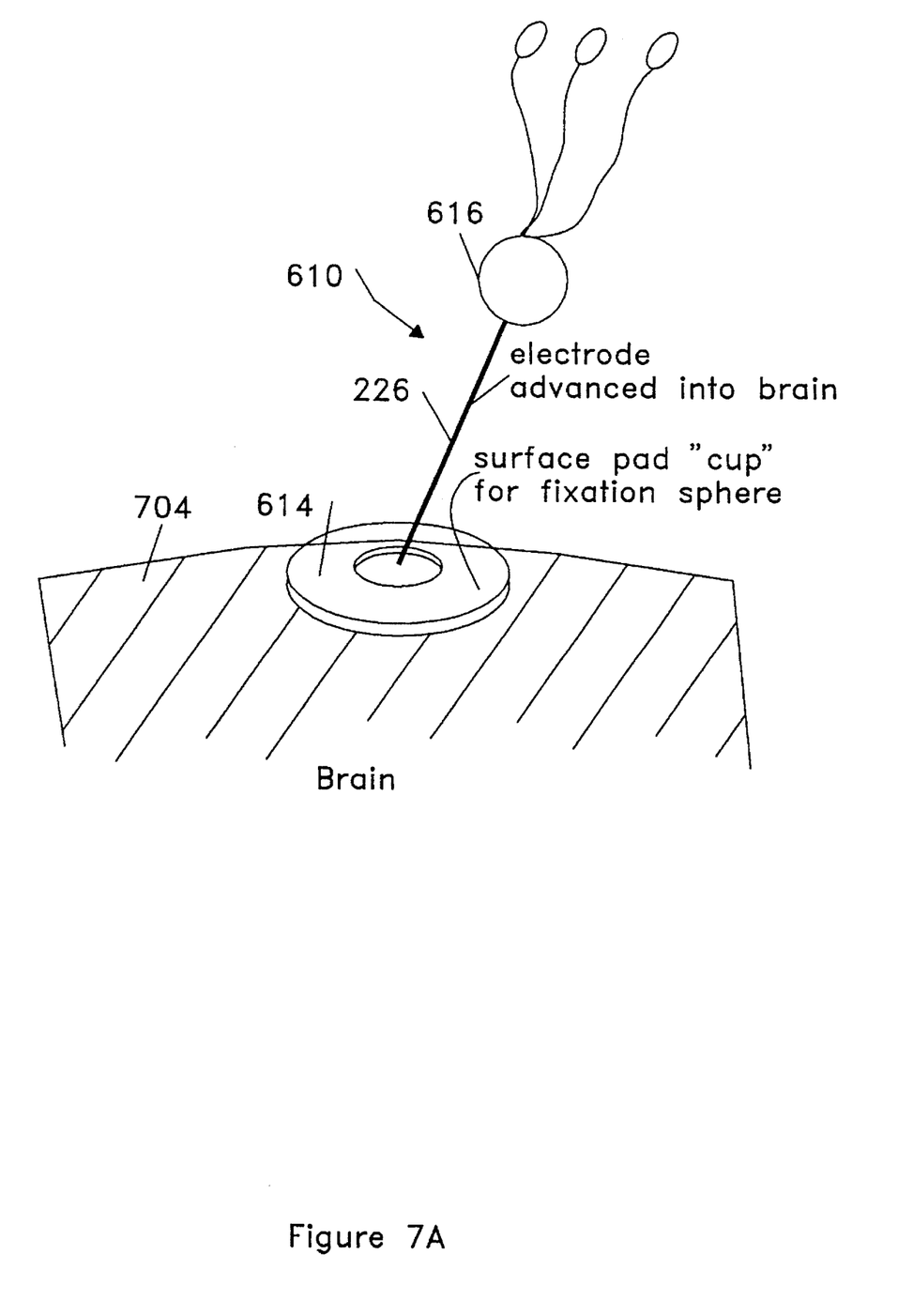
FIG. 7A shows the prosthetic of FIG. 6 as looking down on the patients brain surface.
Figure 7B:
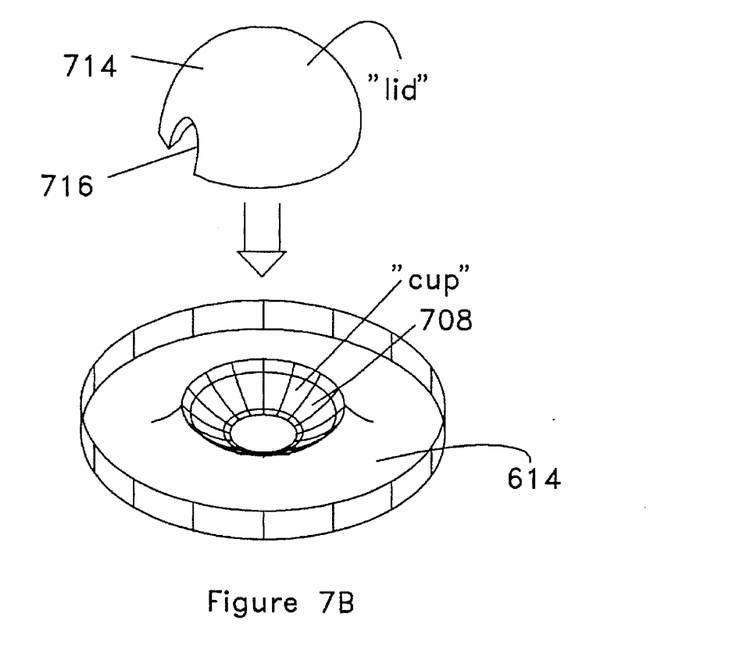
FIG. 7B shows a closer view of a stopping piece with a cup and a lid, and FIG. 7C corresponds to FIG. 7A with the support inserted.
Figure 7C:
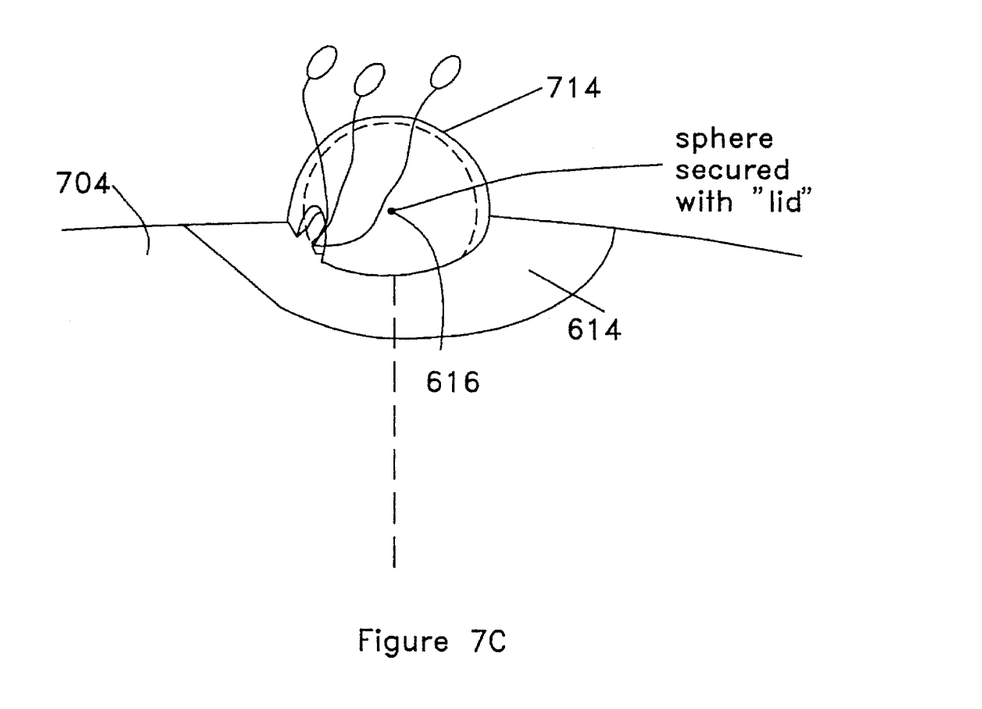

FIG. 7A shows prosthetic 610 of FIG. 6 as looking down on the patients brain surface 704. FIG. 7B shows a closer view of stopping piece 614 with a cup 708 and a lid 714 with a notch 716 for passing leads 232. FIG. 7C corresponds to FIG. 7A with support 226 inserted into surface 704 and sphere 616 resting in cup 708. FIG. 7C also shows lid 716 covering sphere 616 with leads 232 extending out of notch 716.

The Risk Benefit Ratio

The clinical usefulness of an auditory neural prosthetic device depends on several variables, most importantly the risk-benefit ratio for a given device. An ideal device effectively restores hearing without risk to the patient's overall health. Salient features of two types of devices are outlined below.

Since auditory cortex 150 is situated in temporal lobe 156, neurosurgeons expose this portion of the brain routinely during a wide range of operations. In the non-dominant temporal lobe, unlike the brainstem, the auditory region is not surrounded by vital structures. If a patient is diagnosed with an infiltrating tumor of the non-dominant auditory cortex, for example, the neurosurgeon can resect this tissue with very little risk of complication.

Another example is temporal lobe surgery for intractable epilepsy. Most patients who undergo this surgery are in good general health but suffer from seizures periodically. Usually, chronic epilepsy is not a life threatening condition, and many patients have seizures for decades during which time they are able to work and raise families.

Since most forms of epilepsy are medically "tolerable," surgical treatment directed at curing epilepsy is only justified when it is highly effective and carriers with it very low risk of morbidity and mortality. A properly selected patient in good general health has a less than one percent chance of developing a significant neurologic complication following an elective non-dominant temporal lobectomy for intractable epilepsy, and a 70 percent chance of being cured of their seizures. In that setting, the risk-benefit ratio is strongly in the patient's favor. An operation designed exclusively to place a stimulating neural prosthetic electrode onto non-dominant auditory cortex could be carried out under local anesthesia and take less than two hours operating time. This procedure would entail even less medical risk than a standard epilepsy resection.

What is claimed is:

1. A neural prosthetic device for a primary auditory cortex of a patient, comprising:
    a speech processor for receiving and processing audio information and for outputting processed electrical signals;
    a mechanical support arranged in said primary auditory cortex supporting a plurality of electrical contacts, said mechanical support being arranged in said primary auditory cortex and each of said plurality of electrical contacts outputting electrical discharges corresponding to said processed electrical signals; and
    electrical coupling means for electrically coupling said electrical contacts to said speech processor.

2. The neural prosthetic apparatus as claimed in claim 1, wherein said mechanical support is arranged in said primary auditory cortex and said plurality of electrical contacts are arranged such that each of said plurality of electrical contacts stimulate geometrically separate locations of said primary auditory cortex.

3. The neural prosthetic apparatus as claimed in claim 1, wherein said electrical coupling means comprises a plurality of leads respectively coupled to said plurality of electrical contacts.

4. The neural prosthetic apparatus as claimed in claim 1, wherein said mechanical support is a rod.

5. The neural prosthetic apparatus as claimed in claim 1, wherein said electrical contacts are approximately uniformly arranged along said mechanical support.

6. The neural prosthetic apparatus as claimed in claim 1, wherein said electrical contacts are spaced approximately 50 to 150 micrometers apart.

7. The neural prosthetic apparatus as claimed in claim 1, wherein said mechanical support is a flexible mechanical support, further comprising a rigid tube, said flexible mechanical support being inserted in said rigid tube to aid insertion of said mechanical support in said primary auditory cortex.

8. The neural prosthetic apparatus as claimed in claim 1, further comprising:
    at least one additional mechanical support tonotopically arranged in said primary auditory cortex, said at least one additional mechanical support supporting an additional plurality of electrical contacts, each of said additional plurality of electrical contacts outputting additional electrical discharges corresponding to said processed electrical signals, and said electrical coupling means further electrically coupling said additional electrical contacts to said speech processor.

9. The neural prosthetic apparatus as claimed in claim 1, wherein said electrical contacts are approximately uniformly arranged along said mechanical support.

10. The neural prosthetic apparatus as claimed in claim 1, further comprising a stopping piece for holding said mechanical support in place.

11. The neural prosthetic apparatus as claimed in claim 10, further comprising a sphere connected to said electrical coupling means, and said stopping piece having a cup for holding said sphere.

12. The neural prosthetic apparatus as claimed in claim 11, further comprising a lid for covering said sphere once said mechanical support is inserted in said primary cerebral cortex.

13. The neural prosthetic apparatus as claimed in claim 12, wherein said lid has a notch for passing said electrical coupling means.

14. A neural prosthetic apparatus for a primary auditory cortex of a patient, comprising:
    a speech processor for receiving and processing audio information and for outputting processed electrical signals;
    a mechanical support tonotopically arranged along said primary auditory cortex supporting a plurality of electrical contacts approximately uniformly arranged along said mechanical support about 50 to 150 micrometers apart, each of said plurality of electrical contacts independently outputting electrical discharges corresponding to said processed electrical signals; and
    electrical coupling means for electrical coupling said electrical contacts to said speech processor.

15. The neural prosthetic apparatus as claimed in claim 14, further comprising a stopping piece for holding said mechanical support in place.

16. In a neural prosthetic device having a mechanical support for arrangement in a primary auditory cortex of a patient, a method of implanting the mechanical support, comprising the steps of:
    acquiring a 3 dimensional digital image of the patient's brain and storing said 3 dimensional image in a memory of a computer;
    digitally subtracting data from said 3 dimensional digital image to yield a modified 3 dimensional digital image which shows the orientation of said primary auditory cortex in the patient's brain; and
    inserting said mechanical support into said primary auditory cortex using said modified 3 dimensional digital image as a guide.

17. The method as claimed in claim 16, further comprising the steps of:
    repeatedly outputting said processed electrical signals to said plurality of electrical contacts; and
    adjusting the orientation of said mechanical support in said primary auditory cortex as the patient describes effects of said repeatedly outputting step.

18. The method as claimed in claim 17, wherein said repeatedly outputting step comprises outputting signals which cause said primary auditory cortex to be stimulated at geometrically separate locations corresponding to separate auditory tones.

* * * * *